United States Patent [19]

Kirsch

[11] Patent Number: Plant 6,168

[45] Date of Patent: May 3, 1988

[54] LILY PLANT CALLED LITTLE PINK RASCAL

[75] Inventor: Ted T. Kirsch, Myrtle Point, Oreg.

[73] Assignee: Melridge Inc., Gresham, Oreg.

[21] Appl. No.: 861,241

[22] Filed: May 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; W. Dennis Drehkoff

[57] ABSTRACT

A new and distinct lily cultivar of the Oriental hybrid type particularly characterized by its very short stature and its relatively large bowl-shaped flowers of rich magenta-rose coloration borne as a compact raceme, and by its deep rose pink bud coloration before the flowers open, the compact inflorescence being borne on an unusually short peduncle.

1 Drawing Sheet

BACKGROUND OF THE INVENTION

This new lily variety originated as a seedling of unknown parentage discovered by me at my nursery in Arcata, Calif., in June of 1975. The large and richly colored flowers borne on a plant of very short stature and silhouette appropriate for pot plant culture prompted me to propagate this new plant for further evaluation, which was carried on by bulb scale propagation by me and under my direction at Arcata, Calif. This initial propagation appeared to be so satisfactory that propagation through successive generations was carried on both by natural propagation from bulblets and division and by tissue culture originating from bulb scales. The successive generations of this plant produced at Arcata, Calif., have demonstrated that the novel and distinctive characteristics of this variety hold true under asexual propagation from generation to generation and appear to be firmly fixed.

DESCRIPTION OF THE DRAWING

This new variety of lily plant is illustrated by the accompanying photographic drawing, in which the upper view shows the distinctive short silhouette of the plant, as well as its large, richly colored flowers, and the lower view shows a close three-quarter view of one of the flowers, the color rendition being as nearly true as can reasonably be obtained by conventional photographic procedures.

DESCRIPTION OF THE NEW VARIETY

The following is a detailed description of my new variety of Oriental hybrid lily with nomenclature according to The International Lily Register of The Royal Horticultural Society at London, England (1969), and with color designations according to The R.H.S. Colour Chart published in 1966. These observations were made on greenhouse grown plants at Sandy, Oreg., in the spring of 1985.

THE PLANT

Origin: Seedling.
Parentage: Unknown.
Classification:

*Botanic.*—Hubrid lily cultivar, Division VII-B of The Horticultural Classification of Lilies (The Royal Horticultural Society, 1969).

*Commercial.*—Oriental Hybrid Lily.

Form: Single stem, erect and bushy.
Height: About 30 to 50 cm.
Growth: Compact, sturdy and vigorous.
Foliage:

*Quantity.*—Abundant.

*Leaf size.*—Ranging from about 10 cm. long and 2 to 3 cm. wide at the top of the stem to about 5 cm. long and 2 cm. wide at the bottom.

*Leaf shape.*—Broad lanceolate.

*Texture.*—Leathery.

*Aspect.*—Glossy.

*Color.*—Dark green (chlorophyll pigmentation overlaid with anthocyanin).

Bulbs:

*Size.*—Various; up to 30 cm. in circumference depending on age.

*Color.*—White with flushes of soft pink or yellow which deepen as the bulbs become larger or are exposed to light.

THE BUD

Form: Ovoid with obtuse tip.
Size: Averaging about 10 to 12 cm. long and 10 cm. in circumference depending upon light and nutritional levals.
Opening rate: The bud opens slowly in response to morning light. The buds open successively from the lowermost to the uppermost, as is typical of the genus Lilium.
Color: Medium magenta rose RHS 63C-D just before the buds open, shading to softer tones at the tips of the buds and the midribs show soft green coloration about 1 mm. wide, which changes to soft pink on the day the flower opens.
Peduncle: Hardly apparent and usually about 1 cm. long or shorter. The peduncle may elongate under low light conditions or when the bulbs have been improperly stored prior to forcing.

THE FLOWER

Blooming habit: This plant flowers once and profusely in midseason, generally in late July under field conditions in Arcata, Calif. When properly forced from appropriately precooled bulbs, this plant will flower in 95 to 110 days in the greenhouse.

Size: Large, averaging 18 to 20 cm. in diameter, the tepals recurving to make a bloom width of about 15 to 16 cm. Recurved tepals form a bowl about 6 to 6½ cm. deep.

Borne: As a compact raceme 15 cm. long with each pedicel bearing one bud. Bulbs of typical commercial size bear an average of four to eight flowers.

Shape: Bowl shape with broad and overlapping tepals slightly recurved.

Tepalage:

*Number.*—Six.

*Form.*—The tepals are generally ovate with the inner tepals averaging about 4 cm. wide and the outer tepals about 3 cm. wide. The inner tepals overlap slightly and the arrangement is hexagonal.

*Color.*—The basic color of the tepals is red-purple 63C over the inner half of the tepal length shading to 62C-D at the tepal margins and toward the tip end.

*Papillae.*—Copious in the center 12 cm. of each flower, there being about 125 on each inner tepal and about 50 on each outer tepal.

Pedicel:

*Length.*—About 2 to 7 cm.

*Color.*—Dark green.

*Arrangement.*—Ascending and extending angularly at an angle of about 45° from the stem.

Longevity: Tepals stay on the stem about two to three weeks.

Color change: The color fades slightly and becomes more brown as the flower ages or is exposed to intense light and heat. Under cool conditions, the color is richer and retained longer.

Fragrance: Heavy and sweet.

Disease resistance: The flower and plant are adequately resistant to disease as observed in northwest California and western Oregon.

Lasting quality: This flower is long lasting, both on field grown plants and on forced potted plants.

REPRODUCTIVE ORGANS

Stamens:

*Number.*—Six.

*Arrangement.*—Typical of genus Lilium.

Anthers:

*Color.*—178C, occasionally greyed orange 168B-C.

Filaments:

*Length.*—About 7 to 8 cm.

*Color.*—Soft pink to white.

Pistils:

*Number.*—One per flower.

Style:

*Color.*—Light green to white, sometimes slightly pink.

Stigma:

*Color.*—Light green.

Ovary: Typical of genus Lilium.

The short stature of this new lily variety, with its large flowers and relatively broad leaves and good bud color when forced into flower out-of-season, makes this plant a valuable addition to the commercial production of potted lilies, particularly in view of its reliable performance when forced to flower from bulbs which have been dug at the proper stage of maturity and properly precooled, even during periods of low light.

I claim:

1. A new and distinct Oriental hybrid lily, substantially as herein shown and described, characterized by its short stature, its richly colored, outwardly facing flowers of large size, its short, moderately broad leaves of dark green color, and its adaptability as a potted plant cultivar.

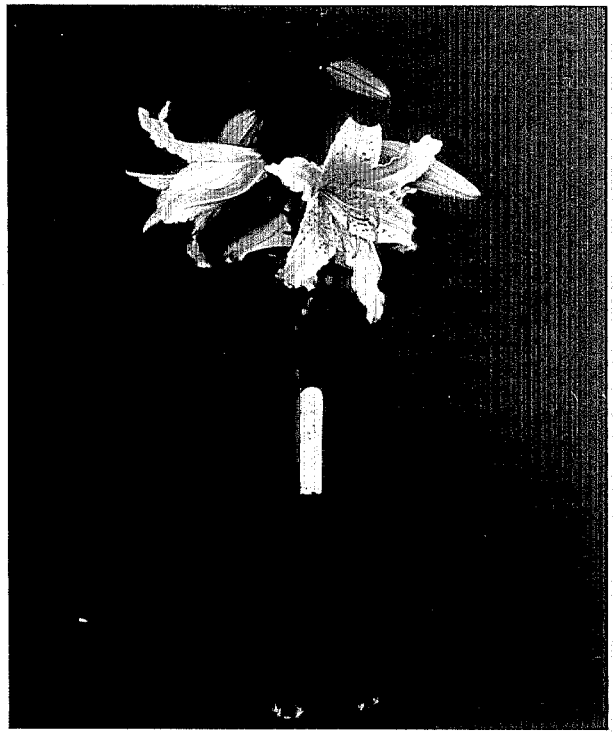
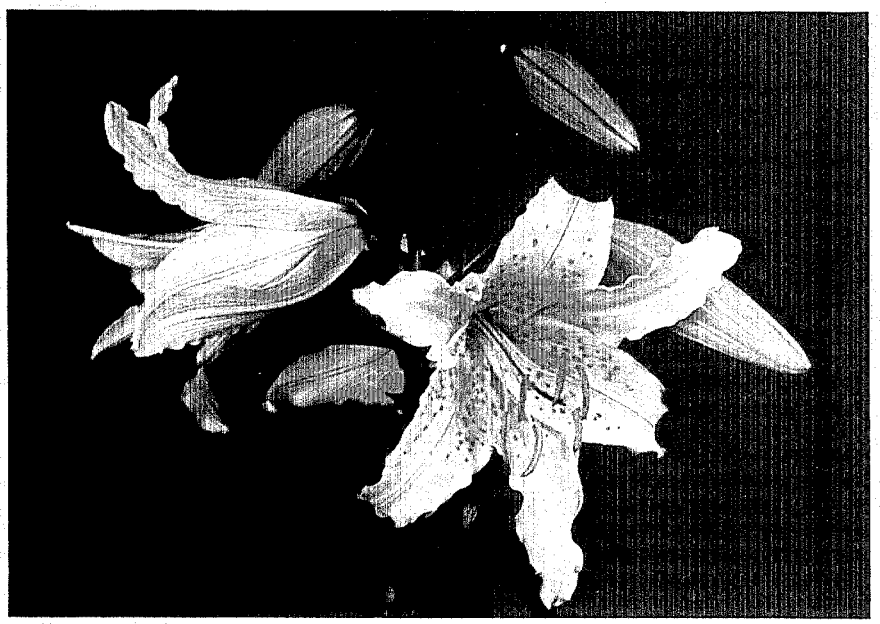

* * * * *